United States Patent [19]

Chen et al.

[11] Patent Number: 5,463,110

[45] Date of Patent: Oct. 31, 1995

[54] MICHAEL ADDUCTS OF N-VINYLFORMAMIDE AND ACRYLIC AND METHACRYLIC ESTERS

[75] Inventors: Ning Chen, Allentown; Walter L. Renz, Macungie; Robert K. Pinschmidt, Jr., Allentown, all of Pa.

[73] Assignee: Air Products and Chemicals, Inc., Allentown, Pa.

[21] Appl. No.: 246,434

[22] Filed: May 20, 1994

[51] Int. Cl.$^6$ ................................................. C07C 229/06
[52] U.S. Cl. ............................................................ 560/172
[58] Field of Search .................................... 560/155, 172

[56] References Cited

U.S. PATENT DOCUMENTS

| | | | |
|---|---|---|---|
| 4,129,709 | 12/1978 | Lorenz et al. | 526/264 |
| 4,205,139 | 5/1980 | Barzynski et al. | 525/38 |
| 4,319,811 | 3/1982 | Tu et al. | 351/166 |
| 4,348,427 | 9/1982 | Priola et al. | |
| 4,424,314 | 1/1984 | Barzynski et al. | 525/454 |
| 4,725,524 | 2/1988 | Elzer et al. | 430/258 |
| 5,281,682 | 1/1994 | Cornforth et al. | 526/273 |

OTHER PUBLICATIONS

Becking, L., Tetrahedron Letters, 29(23), 2797–2800 (1988).
Kurtz and Disselnkotter, –Liebigs Ann. Chem, 764 pp. 69–93 (1972) Enamide.

Primary Examiner—Christopher Henderson
Attorney, Agent, or Firm—Mark L. Rodgers; William F. Marsh

[57] ABSTRACT

Novel unsaturated compounds comprising the 3-(N-vinylformamido)propionates and 2-methyl-3-(N-vinylformamido)propionates are obtained by the Michael addition reaction of N-vinylformamide with an acrylic or methacrylic acid ester. These compounds are useful as monomers in free radical polymerizations, particularly as components of photocurable coatings.

10 Claims, No Drawings

MICHAEL ADDUCTS OF N-VINYLFORMAMIDE AND ACRYLIC AND METHACRYLIC ESTERS

TECHNICAL FIELD OF THE INVENTION

The invention relates to compounds useful as monomers in free radical polymerizations, particularly as components of photocurable coatings.

BACKGROUND OF THE INVENTION

Unsaturated monomers of the N-vinylamide class have been employed in free radical polymerization reactions for the preparation of homopolymers and copolymers having a range of useful properties. Of these, the N-vinyllactams, in particular N-vinyl-2-pyrrolidone, have been employed extensively owing to their wide commercial availability and rapid polymerization with a range of comonomers including the acrylic and methacrylic esters. Polymerizations of other cyclic and acyclic N-alkyl substituted (tertiary) N-vinyl carboxylic acid amides have been described as well. Secondary N-vinylamides such as N-vinylformamide and N-vinylacetamide also copolymerize well with acrylic compounds and are useful for preparing hydrophilic polymers which may be subsequently hydrolyzed to introduce vinylamine functionality.

Several N-vinylamide monomers have been suggested as components of liquid and solid photopolymerizable compositions of various types. As a class, the vinylamides possess certain useful properties for these applications, including good compatibility with other chemistries, copolymerizability with acrylates, comparative resistance to oxygen inhibition, and favorable adhesion-promoting characteristics.

Lorenz et al. U.S. Pat. No. 4,129,709 disclose a coating composition comprising N-vinyl-2-pyrrolidone, an acrylated oligomer, and an acrylic acid ester having a boiling point of at least 200° C. at 760 mm Hg. These compositions may be cured by exposure to actinic radiation between 200 and 750 nm or by an electron beam. Tu et al. U.S. Pat. No. 4,319,811 describe radiation curable coatings consisting of triacrylate or tetraacrylate monomers with an N-vinyl imido monomer, preferably an N-vinyllactam such as N-vinyl-2-pyrrolidone. Priola and coworkers U.S. Pat. No. 4,348,427 describe compositions comprising mixtures of acrylated oligomers and/or unsaturated polyester oligomers with a least one unsaturated compound of the amide, lactam, piperidone and urea classes, and curing them by exposure to ultraviolet radiation in the 200–400 nm range.

Cornforth et al. U.S. Pat. No. 5,281,682 teach improved radiation-curable formulations containing N-vinylformamide and an oligomer selected from the group epoxy acrylates, urethane acrylates, polyester acrylates and mixtures thereof. Elzer et al. U.S. Pat. No. 4,725,524 disclose a dry film photoresist containing an acrylic or methacrylic oligomer, a compatible film-forming water-soluble polymer, one or more compatible photopolymerizable monomers, a photoinitiator, and other additives. Barzynski et al. U.S. Pat. Nos. 4,205,139 and 4,424,314 teach curable compositions containing N-vinyl compounds in which at least two N-vinyl groups are present and in which at least one carbonyl group is bound to the nitrogen of the N-vinyl group, said carbonyl group in turn being bonded to a nitrogen or carbon atom.

The most commercially important class of radiation-curable compositions relies upon the free radical photopolymerization of unsaturated acrylic compounds. These systems are commonly based on acrylic ester-terminated oligomers derived from one of several major resin chemistries, such as urethanes, epoxies, polyesters, and others. The acrylated oligomers are often compounded with various nonpolymerizable materials (pigments, fillers, flow agents, antioxidants, etc), as well as photoinitiators and co-catalysts, and applied to a substrate before curing. Curing is accomplished by exposing the formulation to ultraviolet light or other type of radiation until a dry adherent polymerized film is formed. Formulations of this general description find use as printing inks, protective coatings, adhesives and the like.

In practice, it is often necessary to incorporate diluent monomers into these formulations in order to lower the viscosity of the oligomers sufficiently to permit adequate flow and leveling on the substrate prior to irradiation. This is particularly true of formulations applied by methods common to the printing and coating industries. Diluent monomers used for this purpose fall into two broad categories: multifunctional (or polyunsaturated) types and monofunctional (or monounsaturated) compounds. Multifunctional monomers generally provide high cure speed and high crosslink density, leading to hard, chemically-resistant films, but they may not sufficiently lower viscosity and may also contribute to poor adhesion due to excessive shrinkage of the films on curing. Monofunctional monomers are usually more effective in reducing viscosity, and can yield softer, more extensible films that exhibit better adhesion to many substrates.

Although a large number of unsaturated compounds are potentially useful as diluents, relatively few have proven to be practical. This is because reactive monomers employed in this technology must conform to a number of physical and performance requirements, among them: high fluidity, low vapor pressure, low color, low odor, high flash point, low toxicity and irritancy, broad compatibility and rapid copolymedzability with the other unsaturated species.

Monounsaturated N-vinylamides have the aforementioned useful properties as photocurable compounds, however, few of these monomers meet all the criteria for use as diluents. It is found, for example, that the lower alkyl tertiary N-vinylamides (e.g. N-methyl-N-vinylformamide, N-methyl-N-vinylacetamide) are excellent solvents, but are excessively volatile and possess relatively low flash points (under 200° F.). The higher secondary and tertiary N-vinylamides (e.g. N-vinylacetamide, N-vinylbenzamide, N-vinylcaprolactam, N-phenyl-N-vinylacetamide, N-vinyl-2-piperidinone, N-vinylsuccinimide, N-vinylmorpholinone) are less volatile and less hydrophilic, but have melting points above room temperature, making them less desirable as diluents or coreactants in liquid systems. Many of these monomers exhibit unacceptably slow cure rates as well.

Kurtz and Disselnkoetter *Liebigs Ann. Chem.*, 764, p. 69–93, (1972) describe the preparation of 3-(N-vinylformamido)propionitrile by the reaction of N-vinylformamide with acrylonitrile in benzene utilizing a potassium cyanide catalyst. Applications for the compound are not reported. However, this material has also been found to have certain deficiencies as a photocurable monomer. A further disadvantage is the use of a highly toxic catalyst in its preparation.

Of the N-vinyl class, only N-vinyl-2-pyrrolidone (NVP) has achieved widespread commercial acceptance in the technology owing to its satisfactory combination of good solvent properties, low vapor pressure and high cure rate in liquid photocure systems. More recently, N-vinylformamide (NVF) has been shown to offer equal or superior performance. However, both NVP and NVF have certain disadvantages as well. Notably, both monomers possess relatively high glass transition temperatures (150°–175° C.) which imposes some contraints upon the film properties that can be achieved. In addition, both monomers are relatively hydrophilic which can undesirably increase the water sensitivity of cured films.

It is the object of this invention to provide novel N-vinyl monomers which simultaneously exhibit the desirable solvent and polymerization characteristics of the N-vinylamides, and which also possess the required physical properties necessary to render them practical as components of liquid radiation-curable formulations, and which further possess a wider range of Tg and hydrophobic properties than is exhibited by the preferred liquid monomers of the prior art, i.e. NVP and NVF.

SUMMARY OF THE INVENTION

The present invention relates to unsaturated monomers comprising the 3-(N-vinylformamido)propionates and 2-methyl-3-(N-vinylformamido)propionates obtained from the Michael addition of N-vinylformamide (NVF) to acrylic or methacrylic acid esters. The materials encompassed by this invention have the general structure:

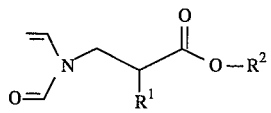

Where $R^1$ is hydrogen or methyl, and $R^2$ is a linear or branched alkyl, cycloalkyl, arylalkyl, alkyloxyalkyl, oligoalkyleneoxy or aryl group containing from 1 to about 20 carbon atoms.

The compounds of the instant invention are prepared by the reaction of N-vinylformamide with the acrylic or methacrylic ester in the presence of a basic catalyst, such as sodium methoxide, sodium ethoxide, or butyllithium. The reaction is performed either in a mixture of the neat monomers, or in a suitable organic solvent, at a temperature between 0° and 100° C. The reaction is allowed to proceed for a period between 2 and 100 hours, after which time the purified product is preferably recovered by vacuum distillation.

Compounds prepared according to this invention have been found to be useful as monomers, especially in photocurable coatings. The compounds demonstrate excellent solvent properties, low viscosity, a wide liquid range, low vapor pressure, low color, excellent color stability, good adhesion and high cure speed in free radical photopolymerization. In addition, the materials defined under the invention may be selected to provide a wide range of Tg and hydrophobic characteristics.

It is recognized by the inventors that, while useful in radiation curing, these monomers may have broader utility in other types of polymer synthesis such as, for example, bulk, suspension, emulsion or solution polymerization, and with comonomers different from those commonly used in radiation-curing (e.g. ethylene, vinyl acetate, vinyl chloride, maleate esters, acrylonitrile, etc.). Therefore, our invention is intended to subsume the homopolymerization or copolymerization of these monomers by any means known in the art.

DETAILED DESCRIPTION OF THE INVENTION

Novel unsaturated monomers comprising the 3-(N-vinylformamido)propionates and 2-methyl-3-(N-vinylformamido)propionates obtained from the Michael addition of N-vinylformamide to an acrylic or methacrylic acid ester. The materials encompassed by this invention have the general structure:

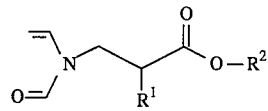

Where $R^1$ is hydrogen or methyl, and $R^2$ is a linear or branched alkyl, cycloalkyl, arylalkyl, alkyloxyalkyl, oligoalkyleneoxy or aryl group containing from 1 to about 20 carbon atoms. In the preferred embodiment, $R^1$ is hydrogen and $R^2$ is a linear or branched alkyl group containing from 1 to 8 carbon atoms.

The subject compounds are readily prepared by the nucleophilic addition of N-vinylformamide (NVF) to an acrylic or methacrylic acid ester. The reaction can be carried out in a simple mixture of the neat monomers, or in a solvent. NVF and the (meth)acrylate ester groups are present in the reaction mixture in molar ratio of from about 1:10 to about 20:1, and preferably at a ratio of about 1.1 moles NVF per equivalent of (meth)acrylate. A free radical inhibitor, such as benzoquinone, is also added. The reaction is preferably carried out in air and at atmospheric or other pressure.

The reaction is conducted in the presence of a strongly basic catalyst such as the alkali or alkaline earth metal or quaternary amine hydroxides or alkoxides. Bases of the methoxide, ethoxide, isopropoxide and t-butoxide class are preferred. Sodium methoxide is especially preferred. Other useful catalysts include the aryl- and alkyllithiums, potassiums and sodiums. The use of other strong bases, such as tertiary amines, amidines or metal amides, such as sodium amide or lithium diisobutylamide is also conceivable, as is the use of anhydrous carbonates. The catalyst is present in the reaction mixture in an amount between about 0.0005 and about 5 wt. %, and preferably between 0.1 and 0.5 wt. % of the total weight of the reactants. In general, the appropriate level of catalyst will vary depending upon the equivalent weight of the (meth)acrylic ester and the molar ratio of the reactants. Following the addition of catalyst, the reactants or reactant solution are maintained at a temperature between 0° and 100° C., and preferably between 20° and 60° C., and allowed to react for a period of from about 2 hours to about 100 hours.

In principle, the reagent monomers can be reacted in batch fashion, via staged addition, or continuously, whichever is most suitable. Synthesis is advantageously performed in a mixture of the neat monomers, however, an inert solvent for both reactants may be employed. Potential solvents include the amides, lower hydrocarbons, chlorinated hydrocarbons, and aromatics. Preferred solvents are esters (e.g. ethyl acetate) and ethers (e.g. ethyl ether, tetrahydrofuran).

The purified 3-(N-vinylformamido)propionate adduct is preferably recovered from the reaction mixture by distillation under vacuum at between 0.01 and about 50 torr. Distillation may be performed either batchwise or continuously as, for example, in a wiped film evaporator. Other possible methods of purification include neutralization of the catalyst followed by vacuum stripping of the unreacted starting materials, or solvent extraction. In some cases, isolation of the 3-(N-vinylformamido) adduct from the reaction mixture may not be required. For example, the crude product may be suitable for applications in which quantities of unreacted NVF and/or (meth)acrylic ester are not problematic.

A wide range of acrylic and methacrylic monomers are potentially useful as the coreactant (or Michael acceptor) in this technology. These include the (meth)acrylic esters of monoalcohols having between 1 and about 20 carbon atoms, such as methyl acrylate, ethyl acrylate, propyl acrylate, n-butyl acrylate, isobutyl acrylate, t-butyl acrylate, cyanoethyl acrylate, N,N-dimethylaminoethyl acrylate, 2-ethoxyethyl acrylate, 2-hydroxyethyl acrylate, hydroxypropyl acrylate, cyclohexyl acrylate, 2-ethylhexyl acrylate, tetrahydrofurfuryl acrylate, octyl/decyl acrylate, isodecyl acrylate, lauryl acrylate, isobornyl acrylate, 2-phenoxyethyl acrylate, methyl methacrylate, and butyl methacrylate.

It will be apparent to those skilled in the art that polymers derived from the (meth)acrylate esters above span a range of properties, such as Tg and hydrophobicity. It has been found that by adducting NVF to an appropriate (meth)acrylic ester, the Tg and hydrophobic properties of the Michael acceptor (i.e. acrylate or methacrylate ester) can be incorporated into the resulting N-vinylamide monomer. Further, it has been found that acrylate esters which are normally too volatile or too flammable for use in radiation curing (e.g. methyl acrylate, butyl acrylate, and ethylhexyl acrylate) can be employed as the Michael acceptor for NVF to yield 3-(N-vinylformamido) adducts that exhibit low volatility and high flash points. The table below compares the physical properties of some 3-(N-vinylformamido)propionates prepared under this invention with N-vinylamides of the prior art.

rated into the formulations, as for example, when they am employed as tinted coatings or inks, or where the formulation is intended to act as a clear varnish over a colored background or graphic. By contrast, the propionate ester adducts of the present invention are essentially colorless as produced and demonstrate excellent resistance to discoloration even after protracted storage at elevated temperatures. A further advantage of the propionate esters is their lower neat viscosity which, as will be shown in the following examples, results in their greater effectiveness in reducing the viscosity of acrylated oligomers.

| Compound | Viscosity (25° C.) | Gardner Color (initial) | Gardner Color (20 days at -20° C.) |
|---|---|---|---|
| Butyl 3-(N-vinylformamido)propionate | 13.5 cps | <1 | <1 |
| 3-(N-vinylformamido)propionitrile | 39.1 cps | 5–6 | 6–7 |

In addition to the monoesters described above, other potential coreactants for N-vinylformamide are the (meth)acrylic esters of polyhydric alcohols. Such higher function-

| Compound | Appearance (25° C.) | Boiling point | Flash point (Cel.)– | Tg (homopoly.) |
|---|---|---|---|---|
| Methyl 3-(N-vinylformamido)-propionate | Colorless liquid | 75° C./0.8 mHg | 124[1] | 24° C. |
| Ethyl 3-(N-vinylformamido)-propionate | Colorless liquid | 88° C./1 mmHg | 124[1] | 46° C. |
| Butyl 3-(N-vinylformamido)-propionate | Colorless liquid | 96° C./0.5 mHg | 98[1] | — |
| t-Butyl 3-(N-vinylformamido)-propionate | Colorless liquid | 80° C./0.5 mmHg | — | — |
| Ethylhexyl 3-(N-vinylformamido)-propionate | Colorless liquid | 122° C./0.8 mHg | — | — |
| Methyl 2-methyl-3-(N-vinylformamido)-propionate | Colorless liquid | 76° C./0.5 mmHg | — | — |
| N-methyl-N-vinylacetamide | Yellow liquid | 70° C./25 mmHg | 58 | — |
| N-vinylformamide | Sl. yellow liquid. | 84° C./10 mmHg | 102 | 150° C. |
| N-vinyl-2-pyrrolidone | Sl. yellow liquid. | 96° C./14 mmHg | 98 | 175° C. |
| 3-(N-vinylformamido)-propionitrile | Yellow liquid | 99° C./1.5 mmHg | ca. 150 | — |

[1]ASTM D-3828

As indicated above, the 3-(N-vinylformamido)propionate esters are colorless liquids at room temperature, exhibit advantageously low volatility, and possess flash points equivalent to or higher than NVF and NVP. Moreover, as evidenced by the examples of the methyl and ethyl propionate esters, adduction of NVF to the corresponding acrylate yields an N-vinyl monomer with a significantly lower homopolymer Tg than the N-vinylformamide starting material.

For comparison, the NVF/acrylonitrile adduct (3-(N-vinylformamido)propionitrile) of the prior art was prepared according to the method of Kurtz and Disselnkoetter. The distilled product was found to be colored and to exhibit poor color stability. Moreover, the color of the propionitrile monomer was found to persist in cured films containing the material. Such coloration is regarded as a disadvantage in this technology since it could interfere with the spectral charactertistics of pigments or dyes which may be incorpoality Michael acceptors include acrylates and methacrylates obtained by esterification of alcohols having hydroxyl functionalities from 2 to about 6. Examples of these compounds include ethyleneglycol diacrylate, 1,4-butanediol diacrylate, hexanediol diacrylate, tripropyleneglycol diacrylate, trimethylolpropane triacrylate, pentaerythritol tetraacrylate, ethyleneglycol dimethacrylate, trimethylolpropane trimethacrylate, polyethyleneglycol dimethacrylate, etc.

The compounds resulting from adduction of NVF to multifunctional (meth)acrylates would possess multiple N-vinyl unsaturation and could be useful as, for example, crosslinking monomers in this technology. In comparision with poly(N-vinyl) monomers of the prior art, these multifunctional propionate esters would be expected to possess a much broader range of attainable properties by varying the chemical composition of the polyalcohol.

In another embodiment of the technology, the NVF/acrylate addition reaction could be extended to include the use of the aforementioned acrylated oligomers as the Michael acceptor. In this case, (meth)acrylated resins of the prior art, such as a polyurethane acrylate or epoxy acrylate oligomers, having an (meth)acrylate functionality of 2 or higher, are reacted with NVF in the presence of a catalyst to produce resins having terminal N-vinyl unsaturation. Such oligomers would range in molecular weight from about 500 to about 8,000, and would be useful as "non-acrylate" film-forming resins in radiation curing.

It is further anticipated that useful N-vinyl compounds may be obtained by reacting NVF with other classes of Michael acceptor monomers, apart from the (meth)acrylate esters described here. Alternative acceptor monomers include any of the materials known in the art to undergo such reactions, such as acrylamide and substituted acrylamides, acrolein, vinyl ketones, vinyl sulfonates, crotonate, fumarate and maleate esters.

In another application of the technology, the 3-(N-vinylformamido)propionate esters provided under this invention may be useful as intermediates in the synthesis of other unsaturated compounds. For example, reactions of carboxylic acid esters could be employed as a method for modifying the compounds to produce other N-vinyl derivatives, such as, for example, hydrolysis of the subject compounds to 3-(N-vinylformamido)propionic acid, or transesterification to produce other mono or higher 3-(N-vinylformamido)propionate esters.

The following examples are intended to better illustrate the invention and are not meant to be limiting.

EXAMPLE 1

Preparation of methyl 3-(N-vinylformamido)propionate.

To a 1000 mL three-neck round bottom flask equipped with a cold water condenser and stirrer was added 215 grams (2.5 moles) of methyl acrylate, 195 grams (2.75 moles) of N-vinylformamide, and 0.1 gram of benzoquinone. The mixture was stirred at ambient temperature for two minutes and 1.5 grams of sodium methoxide was added in one portion. The mixture was stirred for approximately 2 hours at ambient temperature and allowed to stand overnight. The reaction mixture was distilled under vacuum and 361 grams of product (92% yield) boiling at 75° C. (0.8 mm Hg) was collected for analysis. $^1$H NMR analysis confirmed the identity of the 3-(N-vinylformamido) adduct.

EXAMPLE 2

Preparation of ethyl 3-(N-vinylformamido)propionate.

To a 100 mL three-neck round bottom flask equipped with a cold water condenser and stirrer was added 30.9 grams of ethyl acrylate and 21.9 grams of NVF. After mixing for 2 minutes, 0.20 grams of sodium methoxide was added in one portion. The mixture was allowed to react for 3 hours and then distilled to recover 40.3 grams of product boiling at 88° C. (1.0 mm Hg).

EXAMPLE 3

Preparation of butyl 3-(N-vinylformamido)propionate.

72.5 grams of n-butyl acrylate were reacted with 43.0 grams of NVF according to the procedure of Example 2. The mixture was allowed to react for 4 hours and then distilled to recover 101.2 grams of product boiling at 96° C. (0.5 mm Hg).

EXAMPLE 4

Preparation of t-butyl 3-(N-vinylformamido)propionate.

21.9 grams of t-butyl acrylate were reacted with 42.0 grams of NVF according to the procedure of Example 2. The mixture was allowed to react for 72 hours and then distilled to recover 51.5 grams of product boiling at 80° C. (0.5 mm Hg).

EXAMPLE 5

Preparation of ethylhexyl 3-(N-vinylformamido)propionate.

83.1 grams of 2-ethylhexyl acrylate were reacted with 34.4 grams of NVF according to the procedure of Example 2. The mixture was allowed to react for 96 hours and then distilled to recover 79.8 grams of product boiling at 122° C. (0.8 mm Hg).

EXAMPLE 6

Preparation of methyl 2-methyl-3-(N-vinylformamido)propionate.

To a 100 mL three neck round bottom flask equipped with a cold water condenser, oil bath and stirrer was added 33.2 grams of methyl methacrylate and 23.6 grams of NVF. The mixture was stirred at room temperature for 2 minutes and 80 mg of butyllithium (as a 2.5M solution in hexane) was added in a single portion. The reaction mixture was agitated for 8 hours at 65° C. and then distilled to recover 29.5 grams of product boiling at 75°–77° C. (0.5 mm Hg).

EXAMPLE 7

Homopolymerization of methyl 3-(N-vinylformamido)propionate.

The homopolymer of the NVF/methyl acrylate adduct was prepared in order to measure the glass transition temperature of the material. 50 grams of the adduct prepared in Example 1 were added to a reaction vessel, equipped with a stirrer and oil bath, and containing 60 grams of toluene. The mixture was agitated and the temperature raised to 100° C. and 0.5 grams of Vazo™ 88 initiator (1,1'-azobiscyclohexanecarbonitrile) was added in one portion. The reaction was allowed to proceed for 32 hours after which the precipitated polymer was recovered by filtration. The homopolymer was analyzed by gel permeation chromatography and found to have a number average molecular weight (Mn) of 55,600 and a weight average molecular weight (Mw) of 152,100. The glass transition temperature was measured using a differential scanning calorimeter (DSC) and found to be 24° C.

EXAMPLE 8

Homopolymerization of ethyl 3-(N-vinylformamido)propionate.

The homopolymer of NVF/ethyl acrylate adduct was also prepared. 15.1 grams of the adduct prepared in Example 2 was added to a reaction vessel, equipped with a stirrer and oil bath, into which had been placed 13 grams of ethyl acetate. The mixture was agitated and the temperature raised to 80° C., and 0.03 grams of Vazo™ 67 (2,2'-azobis-2-methylbutanenitrile) initiator was added in one portion. The reaction was allowed to proceed for 29 hours after which the polymer was recovered by precipitation into water, filtered and added in a vacuum oven. Analysis by gel permeation chromatography indicated a Mn of 32,300 and a Mw of 106,900. The glass transition temperature as measured by DSC was found to be 46° C.

EXAMPLE 9

Copolymerization of methyl 3-(N-vinylformamido)propionate (NVF/MA) with NVF.

A three neck round bottom flask equipped with a mechanical stirrer, a water condenser, nitrogen inlet/outlet tube and an additional funnel was charged with 15.4 g of NVF/MA, 0.2 g of Vazo 88, and 36.1 g of methoxypropanol. The mixture was heated to 100° C., and stirred at that temperature for 30 minutes. A mixture of 4.6 g of NVF and 0.2 g of Vazo 88 in 10.5 g of methoxypropanol was added through the addition funnel over 40 minutes. The mixture was heated continuously at 100° C. for four hours. A sample withdrawn from the reaction solution was analyzed by GC, which indicated that 76% of the NVF/MA and 98% of the NVF were converted to polymer. The solvent was removed under vacuum and the product was dissolved in $D_2O$. $^{13}C$ NMR analysis showed the expected copolymer with a 40/60 ratio of NVF to NVF/MA.

EXAMPLE 10

Copolymerization of methyl 3-(N-vinylformamido)propionate with butyl acrylate.

A three neck round bottom flask, equipped with a mechanical stirrer, a water condenser, nitrogen inlet/outlet tube and an addition funnel, was charged with 11.5 g of NVF/MA, 0.1 g of Triginox 23, and 20.4 g of methanol. The mixture was heated to 60° C. and stirred at that temperature for 30 minutes. A mixture of 9.4 g of butyl acrylate and 0.1 g of Triginox 23 in 20.1 g of methanol was added through the addition funnel over 3 hours. The mixture was heated continuously at 60° C. for two hours. A sample withdrawn from the reaction solution was analyzed by GC, which indicated that 77% of the NVF/MA and 100% of the butyl acrylate were converted to polymer. The solvent was removed under vacuum and the product was dissolved in DMSO. $^{13}C$ NMR analysis showed the expected copolymer with a 53:47 ratio of butyl acrylate to NVF/MA. The molecular weight of this polymer, determined by GPC (polystyrene as standard), was: Mw=105,485 and Mn=33,616.

EXAMPLE 11

Copolymerization of methyl 3-(N-vinylformamido)propionate with vinyl propionate.

A three neck round bottom flask, equipped with a mechanical stirrer, a water condenser, nitrogen inlet/outlet tube and an additional funnel, was charged with 12.4 g of NVF/MA, 7.9 g of vinyl propionate, and 35.8 g of acetonitrile. The mixture was heated to 60° C., and the mixture was stirred at that temperature for 30 minutes. Triginox 23, 0.2 g, in 10.5 g of acetonitrile was added in one portion to the reaction flask. The mixture was heated continuously at 60° C. for 47 hours. A sample withdrawn from the reaction solution was analyzed by GC, which indicated that 83% of the NVF/MA and 76% of the vinyl propionate were converted to polymer. The solvent was removed under vacuum and the product was dissolved in deutedoacetonitrile. $^{13}C$ NMR analysis showed the expected copolymer with a 50:50 ratio of vinyl propionate to NVF/MA. The molecular weight of this polymer, determined by GPC (polystyrene as standard), was: Mw=19,338 and Mn=8313. The glass transition temperature of this polymer was about 40° C.

EXAMPLE 12

The relative performance of the NVF/acrylate ester adducts as diluents in photopolymerizable compositions was assessed in comparison with N-vinyl monomers of the prior art. Equal weight fractions of the N-vinyl compounds were compared in a model formulation containing an epoxy acrylate oligomer, two multifunctional acrylate monomers and a common free radical photoinitiator.

| Component | Weight % |
|---|---|
| Epoxy diacrylate oligomer[1] | 50% |
| TMPTA[2] | 10% |
| TRPGDA[3] | 10% |
| N-Vinyl Monomer | 30% |
| Irgacure ™ 184[4] | 2.5 phr (based on weight of the above) |

[1]Ebecryl ™ 3700 (UCB Radcure)
[2]Trimethylolpropane triacrylate (UCB Radcure)
[3]Tripropyleneglycol diacrylate (Sartomer SR-306)
[4]1-Hydroxycyclohexyl phenyl ketone (Ciba-Geigy)

The liquid mixtures comprising the oligomer, acrylate monomers, N-vinyl monomer, and photoinitiator were mixed well and the Brookfield viscosity was measured. Thin films were drawn down on cleaned 3"×5" aluminum panels using a #10 wire bar. The panels were cured under ultraviolet light in air using a commercial 300 watt/inch medium pressure mercury lamp and conveyor system. Cured film properties were assessed after a single exposure at a conveyor speed of 105 feet per minute.

The extent of cure was indicated by measuring the water and solvent (methyl ethyl ketone) resistance of the films using the double rub test. Film hardness was evaluated by the Persoz hardness technique using a BYK Gardner Pendulum Hardness Tester calibrated on glass (412 seconds). Relative cure speed of each formulation was evaluated using a depth of cure comparator (UV Process Supply Inc.).

The properties of formulations containing three N-vinyl monomers of the prior art (N-vinylformamide, N-vinyl-2-pyrrolidone and N-methyl-N-vinylacetamide) are listed below:

| | NVF | NVP | NMNVA |
|---|---|---|---|
| Flashpoint (°C.) | 102 | 98 | 58 |
| Formulation viscosity (cps, 25° C.) | 625 | 464 | 212 |
| Persoz hardness (seconds) | 255 | 252 | 178 |
| Depth of cure (mils) | ca. 90 | ca. 90 | ca. 30 |
| Water double rubs | >200 | >200 | >200 |
| MEK double rubs | >200 | >200 | >200 |
| Color of cured film | Colorless | Colorless | Yellow |

As expected, NVF and NVP produced hard, colorless, chemically resistant films, and also exhibited excellent cure speed in this system. NMNVA was most effective in reducing viscosity and produced softer films that retained the yellow color of the monomer. The cure depth of NMNVA was significantly less than the other monomers which is indicative of a slower rate of photopolymerization. In general, a high figure is desirable in this test since it implies that a shorter exposure time, or higher line speed, can be used to cure a given film thickness. NMNVA also had a flash point far below requirements for this application.

Formulations containing the 3-(N-vinylformamido)propionate esters were then evaluated according to the procedure above. Methyl 3-(N-vinylformamido)propionate (abbreviated below as NVF/MA), ethyl 3-(N-vinylformamido)propionate (NVF/EA), and n-butyl 3-(N-vinylformamido)propionate (NVF/BA) were formulated and cured alongside the 3-(N-vinylformamido)propionitrile (NVF/AN) compound of the prior art:

|  | NVF/MA | NVF/EA | NVF/BA | NVF/AN |
| --- | --- | --- | --- | --- |
| Formulation viscosity (cps, 25° C.) | 314 | 1080 | 1250 | 1660 |
| Persoz hardness (seconds) | 159 | 233 | 160 | 219 |
| Depth of cure (mils) | 78 | 70 | 55 | 55 |
| Water double rubs | >200 | >200 | >200 | >200 |
| MEK double rubs | >200 | >200 | >200 | >200 |
| Color of cured film | Colorless | Colorless | Colorless | Yellow |

As shown, all three of the propionate esters were more effective as diluents than the propionitrile adduct. All of the NVF adducts cured to a dry surface in a single exposure to give chemically resistant crosslinked films. The NVF/methyl acrylate adduct gave a lower formulation viscosity than NVF and NVP, produced the softest films and showed excellent cure speed. All of the adducts were observed to reduce the hardness of the films relative to NVF, as would be expected based on their lower Tg values.

The NVF/acrylonitrile adduct produced cured films that retained a strong yellow color. These were measured according to the CIE scale and determined to have a delta-E value of 26 (strongly colored) versus a colorless control (delta-E of 0). All of the NVF/acrylate ester products cured to colorless films.

EXAMPLE 13

The water sensitivity of cured films containing methyl 3-(N-vinylformamido)propionate (NVF/MA) was compared with an identical formulation containing NVF. The formulation used in this test was as follows:

| Component | Weight % |
| --- | --- |
| Urethane diacrylate oligomer[1] | 50% |
| TMPTA[2] | 10% |
| TRPGDA[3] | 10% |
| N-Vinyl Monomer | 30% |
| Irgacure ™ 184[4] | 2.5 phr (based on weight of the above |

[1]Airthane ™ 504 prepolymer capped with 2-hydroxyethyl acrylate (Air Products)
[2]Trimethylolpropane triacrylate (UCB Radcure)
[3]Tripropyleneglycol diacrylate (Sartomer SR-306)
[4]1-Hydroxycyclohexyl phenyl ketone (Ciba-Geigy)

The formulations were cured under the conditions shown in Example 12 and the degree of water sorption of a weighed film was measured after immersion in water for one hour at 60° C. The soaked films were tamped dry with a paper towel, reweighed, and then dried in an oven at 100° C. for two hours. The final weight of the film after oven drying was also recorded. The swell index is defined as the weight ratio of the soaked film to the original starting weight. The % soluble in water is defined as the decrease in weight after oven drying compared to the starting weight. The results of this test are shown below:

|  | NVF | NVF/MA |
| --- | --- | --- |
| Persoz hardness (seconds) | 308 | 167 |
| Water double rubs | >200 | >200 |
| MEK double rubs | >200 | >200 |
| Swell index (water) | 1.2 | 1.0 |
| % Soluble | 7% | 7% |

As shown, the cured film containing methyl 3-(N-vinylformamido)propionate exhibited lower water sorption and was softer than the film containing an equal weight fraction of NVF.

Having thus described the present invention, what is now deemed appropriate for Letters patent is set out in the following appended claims.

We claim:

1. An N-vinyl composition comprising a 3-(N-vinylformamido)propionate represented by the structural formula:

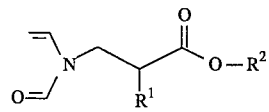

wherein $R^1$ is hydrogen or methyl, and $R^2$ is a linear or branched alkyl group containing from 1 to 8 carbon atoms.

2. The compositions of claim 1 obtained by the base catalyzed addition of N-vinylformamide monomer to an acrylic or methacrylic acid ester.

3. The compositions of claim 2 in which the catalyst is of the alkoxide, alkyl- or aryl-lithium, potassium or sodium class.

4. The composition of claim 2 where $R_1$ is hydrogen and the catalyst is of the alkoxide class.

5. The composition of claim 4 in which the catalyst is sodium methoxide.

6. The composition of claim 4 in which $R_2$ is methyl or ethyl, and the catalyst is sodium methoxide present at between 0.1 and 0.5 wt %.

7. The composition of claim 2 in which $R_1$ is methyl and the catalyst is an alkyl- or aryl-lithium, potassium or sodium compound.

8. The composition of claim 7 in which the catalyst is butyllithium.

9. The composition of claim 7 in which $R_2$ is methyl or ethyl.

10. The composition of claim 9 in which the catalyst is butyllithium present at between 0.05 and 0.2 wt. %.

* * * * *